US00PP35922P2

(12) United States Plant Patent
Trees

(10) Patent No.: US PP35,922 P2
(45) Date of Patent: Jul. 2, 2024

(54) ***BUDDLEIA* PLANT NAMED 'Condappin'**

(50) Latin Name: *Buddleia davidii*
Varietal Denomination: Condappin

(71) Applicant: The Conard Pyle Company, West Grove, PA (US)

(72) Inventor: Scott C. Trees, Arroyo Grande, CA (US)

(73) Assignee: The Conard Pyle Company, West Grove, PA (US)

( * ) Notice: Subject to any disclaimer, the term of this patent is extended or adjusted under 35 U.S.C. 154(b) by 0 days.

(21) Appl. No.: 18/400,331

(22) Filed: Dec. 29, 2023

(51) Int. Cl.
*A01H 6/00* (2018.01)
*A01H 5/00* (2018.01)

(52) U.S. Cl.
USPC ..... Plt./242

(58) Field of Classification Search
USPC ..... Plt./226, 242
See application file for complete search history.

(56) References Cited

U.S. PATENT DOCUMENTS

PP28,836 P2 1/2018 Wood
PP33,845 P2 * 1/2022 Trees ..... Plt./242

* cited by examiner

*Primary Examiner* — Karen M Redden
(74) *Attorney, Agent, or Firm* — Panitch Schwarze Belisario & Nadel LLP; Stephany G. Small; Travis W. Bliss

(57) ABSTRACT

A new and distinct variety of *Buddleia* plant, referred to by its cultivar name, 'Condappin', is disclosed. The new variety displays pink-colored flowers and dark green colored foliage. Attractive moderately vigorous vegetative is formed. The growth habit is compact and well-branched. The new variety is well suited for providing attractive ornamentation in the landscape.

2 Drawing Sheets

Figure 1:
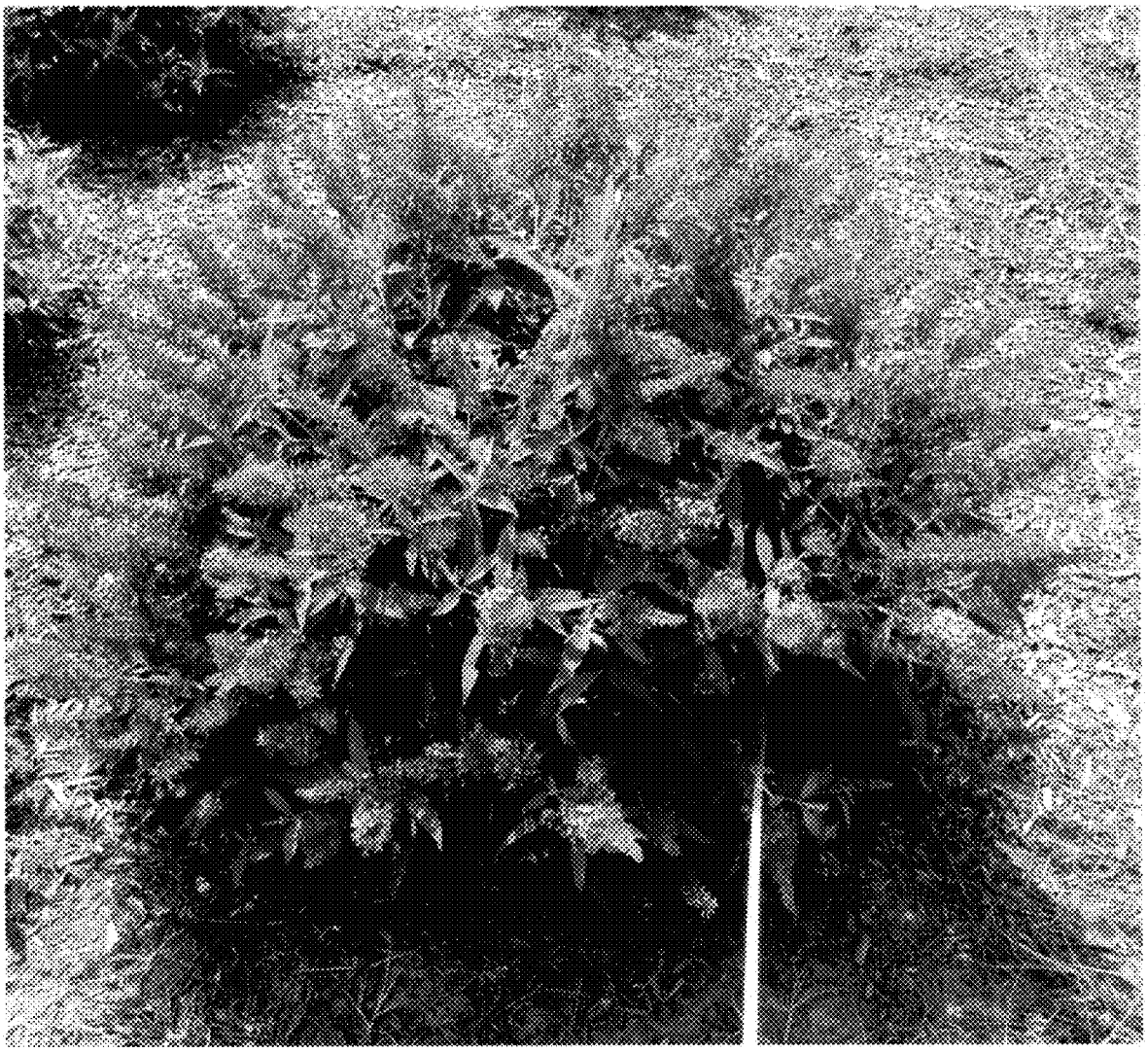

Latin name of genus and species of plant claimed: *Buddleia davidii*.

Variety denomination: 'Condappin'.

STATEMENT REGARDING PRIOR DISCLOSURES BY THE INVENTOR

The first offer for sale of the new variety was January 2023, in Essen, Germany. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of *Buddleia davidii* plant originated through open pollination in Guadalupe, California during 2018. The new cultivar was created by open pollination. The female parent (i.e., the seed parent) was an unnamed breeder seedling variety (not patented). The male parent (i.e., the pollen parent) was unknown.

The seeds resulting from the above open pollination were sown and small plants were obtained which were physically and biologically different from each other. The new cultivar was discovered and selected during 2019 in a controlled environment in Guadalupe, California as a single flowering plant from the progeny resulting from the above-stated open pollination.

The new variety has been found to undergo asexual propagation by terminal stem cuttings. Asexual propagation by terminal stem cuttings in Guadalupe, California has shown that the characteristics of the new variety are stable and are strictly transmissible by such asexual propagation from one generation to another. Accordingly, the new variety undergoes asexual propagation in a true-to-type manner.

SUMMARY OF THE INVENTION

It was found that the new variety of *Buddleia* plant of the present invention:

(a) forms pink-colored flowers,
(b) displays dark green colored foliage, and
(c) exhibits a moderately vigorous, compact, and well-branched growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the female parent unnamed breeding seedling (i.e., the seed parent) displays lavender-pink-colored flowers, whereas the new variety provides pink-colored flowers.

The new variety can also be distinguished from other similar varieties that are commercially available. For instance, the new variety of the present invention can readily be distinguished from the 'SMNBDPT' variety (U.S. Plant Pat. No. 28,836), as the new cultivar displays smaller and more plentiful flower panicles, as compared to plants of the 'SMNBDPT' variety. In addition, the new cultivar provides a more dense and uniform plant habit compared to the 'SMNBDPT' variety.

The new variety has been named 'Condappin'.

BRIEF DESCRIPTION OF THE PHOTOGRAPH

The accompanying photographs show as nearly true as it is reasonably possible to make the same, in a color illustration of this character, typical specimens of the plant and plant parts of the new variety. Colors in the photographs may differ slightly from the color values cited in the detailed description, which accurately describes the colors of the 'Condappin' variety. The photographed plants were approximately two-years-old and grown at Cochranville, Pennsylvania.

FIG.1—illustrates a specimen of the plant grown in the ground outside, displaying the overall growth and flowering habit—side view.

Figure 2:
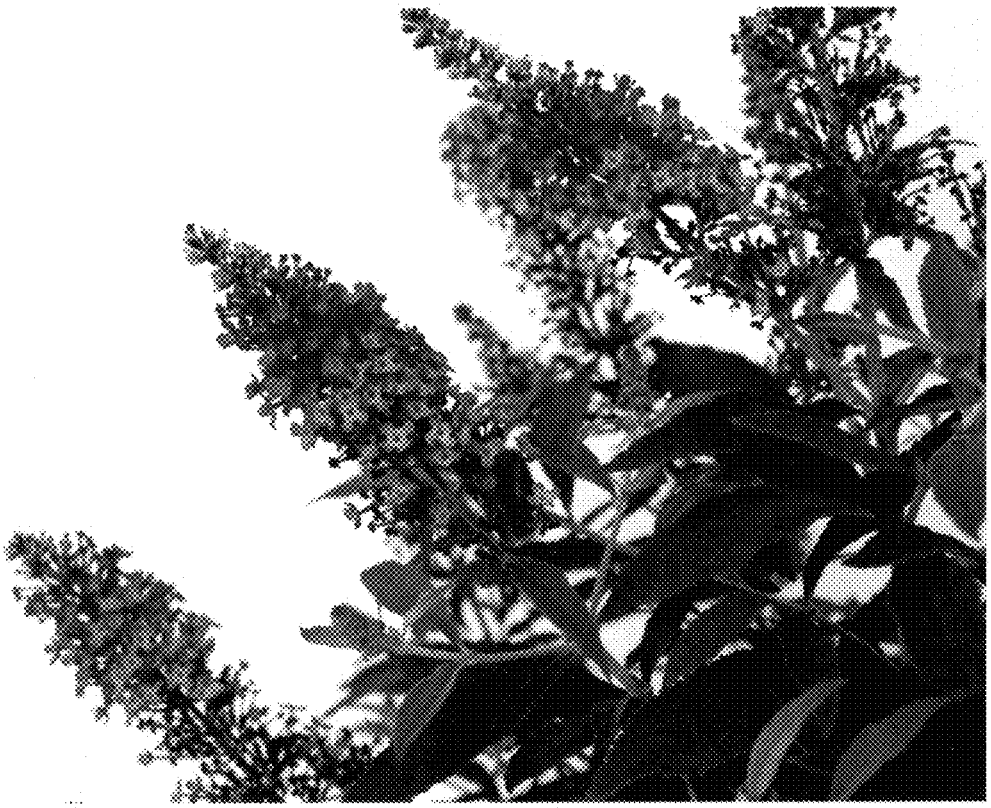

FIG. 2—illustrates a specimen of an inflorescence from a plant of the new variety grown in a 3-gallon container—close-up view.

DETAILED BOTANICAL DESCRIPTION

The chart used in the identification of the colors is that of The Royal Horticultural Society (R.H.S. Color Chart), 2015 edition, London, England. The terminology which precedes reference to the chart has been added to indicate the corresponding color in more common terms and The R.H.S. Colour Chart designation used herein represents the closest color observed on the majority of the specified botanical feature. The color values were determined in July 2023 under natural light conditions in Cochranville, Pennsylvania. The description is based on the observation of plants produced from cuttings from stock plants and grown in three-gallon containers for approximately one year in an outdoor nursery in Cochranville, Pennsylvania. Plants were pinched once after transplant.

Botanical classification: *Buddleia davidii* cultivar 'Condappin'.

Propagation:

*Type cutting*.—Terminal stem.

*Time to initiate roots*.—Approximately 10 to 14 days on average.

*Time to produce a rooted cutting*.—Approximately 21 to 25 days on average.

*Root description*.—Fibrous.

*Rooting habit*.—Freely branching.

Plant:

*Habit*.—Moderately vigorous, compact, and well-branched growth habit.

*Commercial crop time*.—Approximately 2 months from a rooted cutting to finish in a 3-gallon container on average.

*Size*.—Approximately 28.0 cm in height from soil level to top of plant plane on average; and approximately 40.0 cm in width on average.

Branches:

*Branching habit*.—Freely branching, pinching enhances basal branching.

*Quantity of main branches per plant*.—Approximately 8 on average.

*Strength*.—Strong, somewhat flexible, and becomes woody with age.

*Size*.—Length: approximately 24.0 cm on average. Diameter: approximately 4.0 mm on average. Length of central internode: approximately 3.0 cm on average.

*Texture*.—Viscid, densely glandular pubescent.

*Color*.—Young stems: commonly Green Group 139C with some coloring of Brown Group 200B. Mature stems: commonly Greyed-Orange Group 177C.

Foliage:

*Number of leaves*.—Approximately 44 per branch on average; and approximately 10 per branched lateral stem on average.

*Fragrance*.—None detected.

*Form*.—Simple.

*Arrangement*.—Opposite.

*Durability to stress*.—Moderate to high.

Leaves:

*Aspect*.—Primarily perpendicular to stem.

*Shape*.—General: lanceolate to oblanceolate. Margin: serrulate. Apex: acute. Base: attenuate.

*Venation*.—Pattern: pinnate, reticulate.

*Size*.—Length of mature leaf: approximately 10.5 cm on average. Width of mature leaf: approximately 2.5 cm on average.

*Texture*.—Upper and lower surfaces: pubescent.

*Color*.—Upper surface of mature foliage: commonly a color between Green Group 138A and 138B. Lower surface of mature foliage: commonly Greyed-Green Group 194A.

*Petiole*.—Shape: rounded, slightly curved. Length: approximately 3.0 mm on average. Width: approximately 3.0 mm on average. Texture: densely pubescent with lanulose hairs. Color: commonly Greyed-Green Group 192B.

Inflorescence:

*Quantity*.—Approximately 18 open inflorescences per plant on average; and approximately 500 flowers per inflorescence opening from base to apex.

*Type*.—Terminal panicles, each panicle having about 2 to 4 branches on average; and flowers persistent, facing upward and outward.

*Fragrance*.—Very faint.

*Shape*.—Conical.

*Depth or height*.—Approximately 14.0 cm on average.

*Width*.—Approximately 3.5 cm on average.

*Rachis*.—Strength: strong. Length: approximately 10.0 cm on average. Diameter: approximately 2.0 mm on average. Texture: pubescent with stellate hairs. Color: commonly Yellow-Green Group 146C.

Flower:

*Type*.—Single, salverform.

*Bud just before opening*.—Shape: oblong. Length: approximately 6.0 mm on average. Diameter: approximately 1.0 mm on average. Texture: glabrous. Color of petals: commonly Purple Group 77C.

*Corolla*.—Shape: rotate, commonly 4 petals arranged in a single whorl. Depth: approximately 1.0 cm on average. Width: approximately 6.0 mm on average.

*Petals*.—Shape: rotund. Margin: erosulate. Apex: rounded. Length from throat: approximately 8.0 mm on average. Width: approximately 3.0 mm on average. Texture of upper and lower surfaces: glabrous. Color of upper and lower surfaces when first and fully open: commonly Purple-Violet Group N81A.

*Corolla tube*.—Length: approximately 6.0 mm on average. Width: approximately 1.0 mm on average. Diameter of throat opening: approximately 1.0 mm on average. Inner surface: texture is lightly pubescent and color is commonly Greyed-Yellow Group 162A. Outer surface: texture is glabrous and color is commonly Greyed-Yellow Group 162B.

*Calyx*.—Shape: tubular. Length: approximately 3.0 mm on average. Diameter: approximately 1.0 mm on average.

*Sepals*.—Quantity per flower: commonly 4 on average, fused at base. Length: approximately 3.0 mm on average. Width: commonly less than 1.0 mm. Apex: acute. Margin of free portion: entire. Inner surface: Texture: glabrous. Color: commonly Yellow-Green Group 144A. Outer surface: Texture: moderately pubescent. Color: commonly Yellow-Green Group 144A.

*Pedicels*.—Strength: strong, flexible. Length: approximately 1.0 mm on average. Diameter: approximately 3.0 mm on average. Texture: densely pubescent with stellate hairs. Color: commonly Green Group 139C.

*Reproductive organs*.—Androecium: Stamen: commonly 4 per flower, completely adnate to corolla. Anther: shape is lanceolate; length is approximately 1.0 mm on average; and color is commonly Yellow Group 13A. Pollen: amount is moderate; coloration is commonly Yellow Group 13C. Gynoecium: Pistil: commonly 1 per flower; length is approximately 2.0 mm on average. Stigma: shape is cleft, two-parted; length is approximately 1.0 mm on average; color is commonly Yellow-Green Group 144A. Style: length is approximately 1.0 mm; color is commonly Yellow-Green Group 145B, opaque. Ovary: length is approximately 1.5 mm; color is commonly Yellow-Green Group 145A. Seed and fruit: none have been observed to date.

Development:

*Blooming*.—Freely flowering under outdoor growing conditions with substantially continuous blooming from late spring through mid-fall.

*Lastingness of individual flower*.—Approximately 5 days on average.

*Tolerance to disease and pest*.—Not observed to date.

The new 'Condappin' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of *Buddleia* plant named 'Condappin' characterized by the following combination of characteristics:

(a) forms pink-colored flowers, (b) displays dark green colored foliage, and (c) exhibits a moderately vigorous, compact, and well-branched growth habit;

substantially as herein shown and described.

* * * * *